(12) United States Patent
Herlihy et al.

(10) Patent No.: US 7,166,647 B2
(45) Date of Patent: Jan. 23, 2007

(54) MULTI-FUNCTIONAL PHOTOINITIATORS

(75) Inventors: Shaun Lawrence Herlihy, Chatham (GB); Roger Edward Burrows, Casaletto Vapiro (IT); Robert Stephen Davidson, London (GB)

(73) Assignee: Sun Chemical Corporation, Parsippany, NJ (US)

( * ) Notice: Subject to any disclaimer, the term of this patent is extended or adjusted under 35 U.S.C. 154(b) by 16 days.

(21) Appl. No.: 10/492,469

(22) PCT Filed: Sep. 24, 2002

(86) PCT No.: PCT/GB02/04329

§ 371 (c)(1),
(2), (4) Date: Oct. 15, 2004

(87) PCT Pub. No.: WO03/033452

PCT Pub. Date: Apr. 24, 2003

(65) Prior Publication Data

US 2005/0037277 A1 Feb. 17, 2005

(30) Foreign Application Priority Data

Oct. 18, 2001 (GB) .................................. 0125099.2

(51) Int. Cl.
*C07C 69/712* (2006.01)
*C09D 11/10* (2006.01)
*C08F 2/50* (2006.01)
(52) U.S. Cl. .......................... 522/20; 522/905; 522/35; 522/36; 560/52
(58) Field of Classification Search .................. 560/52; 522/905, 35, 36, 20
See application file for complete search history.

(56) References Cited

FOREIGN PATENT DOCUMENTS

| JP | 6263812 A | 9/1994 |
|---|---|---|
| WO | WO 93/16131 | 8/1993 |
| WO | WO 97/07161 | 2/1997 |
| WO | WO 97/49664 | 12/1997 |

*Primary Examiner*—Cynthia Hamilton
(74) *Attorney, Agent, or Firm*—Kramer Levin Naftalis & Frankel LLP

(57) ABSTRACT

Compounds of formula (I):

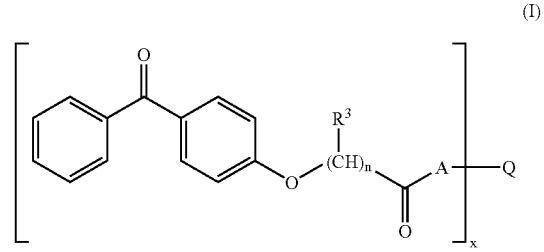

{where n is a number from 1 to 6; $R^3$ is hydrogen, methyl or ethyl; A represents a group of formula $-[O(CHR^2CHR^1)_a]_y-$, $-[O(CH_2)_bCO]_y-$, or $-[O(CH_2)_bCO]_{(y-1)}-[O(CHR^2CHR^1)_a]-$ (where one of $R^1$ and $R^2$ is hydrogen and the other is hydrogen, methyl or ethyl); a is from 1 to 2; b is from 4 to 5; y is from 3 to 10; Q is a residue of a polyhydroxy compound having 2 to 6 hydroxy groups; and x is greater than 1 but no greater than the number of available hydroxyl groups in Q} and esters thereof are useful as photoinitiators for the preparation of energy-curable compositions, such as varnishes and printing inks.

21 Claims, 1 Drawing Sheet

MULTI-FUNCTIONAL PHOTOINITIATORS

The present invention relates to a series of novel compounds which are useful as multi-functional photoinitiators, and which may be used in various coating compositions, including varnishes, lacquers, printing inks and the like, especially varnishes. The invention also provides radiation-curable surface coating compositions which include at least one of the compounds of the present invention as a photoinitiator.

The compounds of the present invention comprise a polymeric core based on a polyhydroxy polymeric compound which is chemically bonded to two or more groups derived from benzophenone or an analogue thereof.

Photoinitiators used in varnish formulations need to have good cure speed, and particularly good surface curing activity, low odour, low yellowing and good solubility. Moreover, as consumers become increasingly wary of extraneous compounds in foodstuffs, in order to comply with likely future legislation, the tendency of the compounds to migrate and be extracted should also be low. Furthermore, in order for the compounds to be useful in practice, it is necessary that they should be preparable with ease and economically on a commercial scale. Thus, one requirement is that, in the course of preparation of the compounds, the reaction rates should be relatively fast. It is becoming increasingly difficult to meet all of these requirements.

At present, benzophenone is by far the most widely used photoinitiator for ultraviolet (UV)-cured overprint varnishes as it has good surface curing, low yellowing and good solubility. It is also very cheap and widely available. However, benzophenone is also known for its relatively strong odour and its exceptional ability to migrate and be extracted from print into foodstuffs, even through barrier packaging such as board and plastic wrappers.

Commonly used benzophenone alternatives for low odour applications include benzophenone-2-methyl ester (Speedcure MBB ex Lambson) and acrylated benzophenone (IRR261 ex UCB), although both of these materials are less efficient than benzophenone. Other less commonly used alternatives include alkyl derivatives such as 4-methylbenzophenone and 2,4,6-trimethylbenzophenone, although these still have some odour on cure. Also, phenylbenzophenone and diphenoxybenzophenones are particularly efficient, but suffer from poor solubility and, in the case of phenylbenzophenone, increased yellowing, which means that it may be used in printing inks (which contain pigments and so can be formulated to hide the yellowing) but that it cannot be used in varnishes.

It is clear that there is a need for a low odour benzophenone derivative with good reactivity, particularly good surface curing, and a limited tendency to migrate and be extracted and which does not yellow on cure and so can be used in varnishes.

It is well known that polymeric benzophenone derivatives and multifunctional benzophenone derivatives will give rise to systems that have low odour and reduced tendency to migrate and be extracted. The disadvantage with many of these systems is that their reduced chromophore content per gram means they have poor cure speed in comparison with benzophenone.

The cure speed of benzophenone derivatives can be related to some degree to their UV absorption spectra. In particular, commercially available benzophenone alternatives, such as MBB and acrylated benzophenone, have an absorption maximum that is shifted to shorter wavelengths than benzophenone as a result of the ester group attached directly to the phenyl ring. In contrast, phenylbenzophenone is highly efficient and has a strong absorption band in the mid-UVB region. Despite being widely used in the curing of inks, phenylbenzophenone cannot be used as a benzophenone alternative in varnishes as it has insufficient solubility and excessive yellowing on cure.

Another material that has a shifted absorption maximum similar to that of phenylbenzophenone is 4-hydroxybenzophenone. This material cannot be used in inks and varnishes directly as it has extremely poor solubility in UV formulations.

It can be seen, therefore, that there is a need for a multifunctional photoinitiator which has a high functionality, good solubility in coating formulations, high reactivity and which gives rise to cured coatings which have extremely low odour, low yellowing, and are likely to have a much lower tendency to migrate and be extracted than most benzophenone alternatives.

We have now discovered a series of multi-functional compounds based on 4-hydroxybenzophenone as a starting material which meet these requirements. The multifunctional nature of the material keeps the functionality per gram relatively high and the polymeric linking group renders the material highly soluble in coating formulations, especially UV-curable formulations. The final product in some cases has a reactivity almost equivalent to benzophenone itself, and in most cases significantly higher than the commonly used benzophenone alternatives. The product is also a liquid which is compatible with UV curing formulations and gives rise to overprint varnishes which have extremely low odour, low yellowing, and are likely to have a much lower tendency to migrate and be extracted than most benzophenone alternatives.

Photoinitiator reactivity per gram is very important in varnish curing. If a material is less reactive than benzophenone it can be added at higher levels to maintain the cure speed of a formulation but only to a limited extent. Above a concentration of 10–12% non-acrylate functional materials either start to behave as plasticisers, as in the case of many aminoacrylate synergists, or just reduce the crosslink density of the cured film to a point where its mechanical properties are impaired. This effect can be countered to some extent by using high functionality acrylate monomers, such as dipentaerythritol pentaacrylate, to increase the crosslink density, but costs will rise dramatically and formulation flexibility will be lost if this approach is taken. For this reason it is important to keep the "polymeric" portion of the molecule as small as possible in order to maximise reactivity whilst still gaining the advantage of ease of incorporation into a formulation.

The tendency of Type II (hydrogen abstraction) photoinitiators to migrate or be extracted from the cured film is in theory higher than for Type I (cleavage) photoinitiators. This is because cleavage photoinitiators generate two highly reactive free radicals which tend to be bound into the cured film by reacting with an acrylate group. Hydrogen abstraction photoinitiators also produce two free radicals in a bimolecular reaction with an amine synergist. Of these, the aminoalkyl radical is highly reactive and binds into the cured film by reacting with an acrylate group, but the ketyl radical has a low reactivity towards acrylate bonds and undergoes termination reactions, or else oxidises back to the ketone. Solvent extraction of a cured film never recovers all of the Type II photoinitiator used, so by whatever mechanism, these materials are capable of becoming bound into the cured film. The tendency to migrate and be extracted can therefore be minimised for both photoinitiator types by increasing the functionality, i.e. by using multifunctional rather than monofunctional photoinitiators.

The tendency of a material to be extracted from a cured film will also depend to some extent on the solvent (simulant) used for the extraction process. Food simulants currently approved in Europe are water (soft drinks and milk), 10% ethanol in water (wine), 3% acetic acid in water (fruit juice) and either olive oil, 95% ethanol in water or isooctane (fatty foods). Since most of these simulants are water based, a photoinitiator should also not be water-soluble in order to achieve the lowest extraction levels. Water insolubility is also important for photoinitiators used in lithographic inks because otherwise they may dissolve in the fount solution and be removed from the ink before the curing stage. Limited water solubility may also disrupt the ink/fount balance, leading to poor printing performance.

WO 93/16131 discloses compounds similar to those of the present invention for use as photo-cross-linking agents or photosensitisers for the cross-linking of elastomers. However, these differ from the compounds of the present invention in the nature of the 'core' compound to which the functional groups are attached, and, as a result, most of those compounds which are disclosed in WO 93/16131 and which have some similarity to the compounds of the present invention are solids, which is undesirable for use in energy-curable coating compositions. Moreover, it is said that the 'core' should not contain readily abstractable hydrogen atoms, for reasons peculiar to the industrial field in which these compounds are intended to be used, unlike the compounds of the present invention.

WO 97/07161 likewise is based on non-polymeric core compounds and requires that these should not contain readily abstractable hydrogen atoms.

U.S. Pat. No. 4,177,122 discloses photoinitiators containing groups derived from benzophenone compounds. However, unlike the polyfunctional compounds of the present invention, the prior compounds are monofunctional with respect to photoinitiator groups and the core compound, unlike that in the compounds of the present invention, is not polymeric. The relatively low photoinitiator content per gram of these compounds will result in them having a poor cure speed. They will also tend to be water-soluble to some degree.

WO 97/49664 discloses a series of photoinitiators including some based on benzophenone and including a polymeric portion. However, these are all mono-functional initiators and suffer the disadvantages already described.

Figure 1:
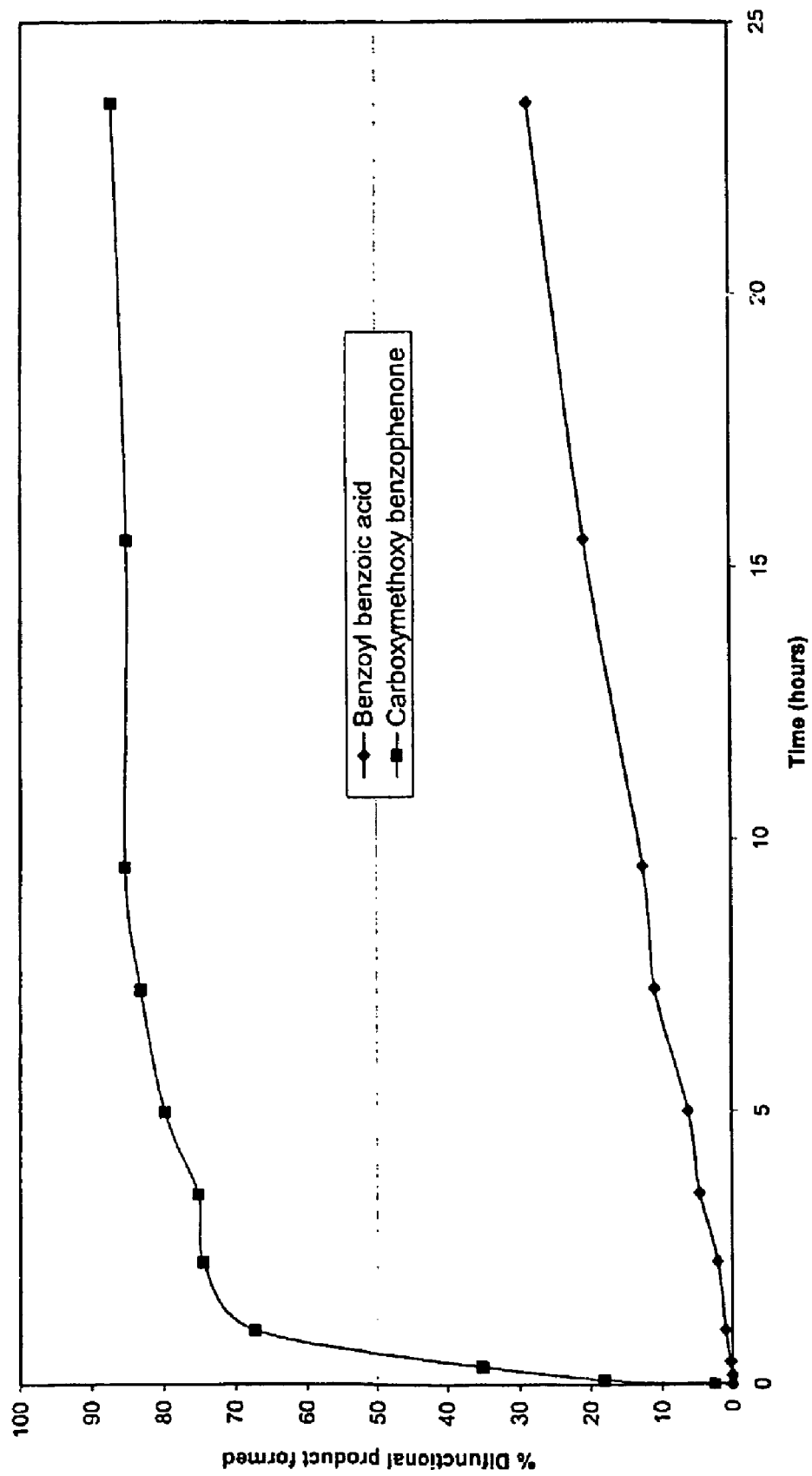
FIG. 1 shows a graph of the formation of the difunctional esterified product for each benzophenone acid type.

Thus, the present invention consists in photoinitiator compounds of formula (I):

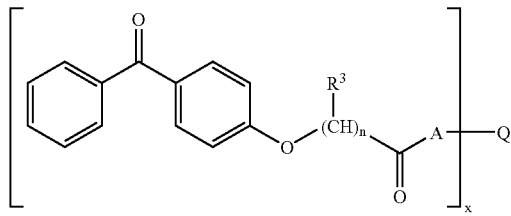

(I)

{where:

n is a number from 1 to 6

$R^3$ represents a hydrogen atom, a methyl group or an ethyl group, and, when n is greater than 1, the groups or atoms represented by $R^3$ may be the same as or different from each other;

A represents a group of formula —[O(CHR$^2$CHR$^1$)$_a$]$_y$—, —[O(CH$_2$)$_b$CO]$_y$—, or —[O(CH$_2$)$_b$CO]$_{(y-1)}$—[O(CHR$^2$CHR$^1$)$_a$]—, where:

one of $R^1$ and $R^2$ represents a hydrogen atom and the other represents a hydrogen atom, a methyl group or an ethyl group;

a is a number from 1 to 2;

b is a number from 4 to 5;

Q is a residue of a polyhydroxy compound having 2 to 6 hydroxy groups; and x is a number greater than 1 but no greater than the number of available hydroxyl groups in Q;

when x is a number greater than 1 but no greater than 2, y is a number from 1 to 10;

or when x is a number greater than 2, y is a number from 3 to 10};

and esters thereof.

These compounds are useful as photoinitiators for use in energy, e.g. UV, curable coating compositions, including varnishes, lacquers and printing inks, most especially varnishes.

Accordingly, the present invention also provides an energy curable liquid composition, comprising:

(a) a polymerisable component which is at least one ethylenically unsaturated monomer or oligomer; and (b) a photoinitiator according to the present invention.

The invention still further provides a process for preparing a cured polymeric composition by exposing a composition of the present invention to radiation, preferably ultra-violet radiation.

Of these compounds, we prefer those in which n is 1, and particularly those in which n is 1 and $R^3$ represents a hydrogen atom.

Alternatively, when n is a number from 2 to 6, we prefer that one group $R^3$ represents a hydrogen atom, or a methyl or ethyl group and the other or others of $R^3$ represent hydrogen atoms.

Particularly preferred compounds are those in which x is 2 and y is a number from 1 to 10.

In the compounds of the present invention, we prefer that A should represent a group of formula —[O(CHR$^2$CHR$^1$)$_a$]$_y$— where a is an integer from 1 to 2, and y is as defined above, preferably a number from 3 to 10, more preferably A represernts a group of formula —[OCH$_2$CH$_2$]$_y$—, —[OCH$_2$CH$_2$CH$_2$CH$_2$]$_y$—or —[ OCH(CH$_3$)CH$_2$]$_y$—, where y is as defined above, preferably a number from 3 to 10, or a group of formula —[O(CH$_2$)$_b$CO]$_y$—or —[O(CH$_2$)$_b$CO]$_{(y-1)}$—[O(CHR$^2$CHR$^1$)$_a$]$_y$—, from 4 to 5 and y is as defined above, preferably a number from 3 to 10. Still more preferably, y is a number from 3 to 6.

It is a feature of the present invention that the compounds are of a generally polymeric nature. The polymeric nature may be provided by either the group represented by Q or the group represented by A or by both.

The polymeric polyhydroxy residue of formula Q—(A—)$_x$, which forms the core of the compounds of the present invention, has a major influence on the behaviour of the compounds. In accordance with the present invention, it is important that it should have a polymeric nature, since the resulting compounds tend to be liquid or of low melting point, thus aiding dispersion in the coating composition. Compounds having a similar structure but not polymeric tend to be solid and/or insoluble in these coating compositions. However, we prefer that the core residue, of formula $Q-(A-)_x$, should not have too high a molecular weight, and prefer that the residue of formula $Q-(A-)_x$ should have a molecular weight no greater than 2000, preferably no greater than 1200, still more preferably no greater than 1000, and most preferably no greater than 800.

We particularly prefer that Q should be a residue of ethylene glycol, propylene glycol, butylene glycol, glycerol, trimethylolpropane, di-trimethylolpropane, pentaerythritol or di-pentaerythritol.

When x is a number less than the number of available hydroxy groups in the compound of which Q is the residue, it will be appreciated that the compounds of the present invention may have free hydroxy groups. If desired, or if preparation of the compounds is effected in the presence of an acid, these hydroxy groups may be esterified. There is no particular restriction on the nature of the esters so prepared, although simple, e.g. lower fatty acid, esters are preferred, such as the $C_2$–$C_6$ alkanoyl esters. Examples of such esters include the acetate, propionate, butyrate and valerate esters.

It will be appreciated that, when the compounds of the present invention are analysed, the numbers a, b and y in the above formulae need not be integral, and, indeed, it is unlikely that they will be integral, since the compounds of the present invention may be mixtures of several compounds in which the numbers a, b and y differ. In accordance with the present invention, provided that the average value of each of these numbers is as defined above, this will be satisfactory. Of course, for each individual molecule of the compounds of the present invention, a, b and y will be integral, and it might be possible to separate out such individual compounds, but, in practice, mixtures of these compounds are used.

The compounds of the present invention may be prepared by reactions well known for the preparation of compounds of this type, the exact reaction route chosen depending upon the nature of the compound which it is desired to prepare.

For example, the compounds may be prepared by reacting a 4-carboxyalkoxybenzophenone of formula (II):

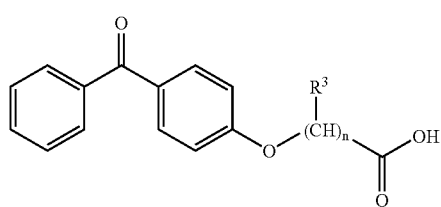

(II)

(where n and $R^3$ are as defined above), such as 4-carboxymethoxybenzophenone, with a core compound of formula (III):

(III)

where A, x and Q are as defined above.

The reaction is normally and preferably effected in the presence of a solvent, the nature of which is not critical to the present invention, provided that it has no adverse effect on the reagents or on the reaction. Examples of suitable solvents include: aromatic hydrocarbons, such as benzene, toluene or xylene.

The reaction is preferably effected in the presence of an acidic catalyst, for example: a sulphonic acid, such as p-toluenesulphonic acid or methanesulphonic acid; a mineral acid, such as sulphuric, hydrochloric or phosphoric acid; or a Lewis acid, such as aluminium chloride, boron trifluoride or an organotitanate.

The temperature at which the reaction is carried out is likewise not critical to the present invention and may vary widely, depending on the reaction conditions and the nature of the reagents and solvent, provided that it is sufficiently high that the water formed in the course of the reaction is removed, in order to drive the reaction to completion. We therefore generally find it convenient to carry out the reaction at about the reflux temperature of the reaction mixture. The time required for the reaction may also vary widely, depending mainly on the reaction temperature. However, under the preferred conditions outlined above, a period of from 1 to 20 hours will normally suffice.

When the reaction is complete, the desired product may be removed from the reaction mixture by conventional means, for example by washing the reaction mixture, e.g. with water and/or and aqueous alkali, drying and then removing the solvent by evaporation under reduced pressure.

Although the compounds of the present invention are especially useful as photoinitiators for use in the production of varnishes, they may also be used with advantage in many other kinds of energy-curable coating compositions. For example, although yellowing is not such a problem with printing inks, it may still be advantageous to have a photoinitiator which does not result in yellowing on cure or on ageing, since this gives the ink formulator a much greater degree of freedom in choosing the other ingredients of the ink, including the pigment.

A coating composition incorporating the compounds of the present invention will normally comprise at least one radiation-curable monomer and/or oligomer, the compound of the present invention and possibly an additional reactive diluent. In the case of a printing ink, the composition will also contain a colorant, e.g. a pigment. The radiation-curable monomer or oligomer is preferably an ethylenically unsaturated compound. Examples of suitable acrylate oligomers include aliphatic or aromatic urethane acrylates, polyether acrylates, polyester acrylates and epoxy acrylates (such as bisphenol A epoxy acrylate). Examples of suitable acrylate monomers include hexanediol diacrylate, trimethylolpropane triacrylate, di-trimethylolpropane tetra-acrylate, di-pentaerythritol pentaacrylate, polyether acrylates, such as ethoxylated trimethylol propane triacrylate, glycerol propoxylate triacrylate, ethoxylated pentaerythritol tetraacrylate, and epoxy acrylates such as dianol diacrylate (=the diacrylate of 2,2-bis[4-(2-hydroxyethoxy)phenyl]propane, Ebecryl 150 from UCB) and glycol diacrylates such as tripropylene glycol diacrylate.

Also, the compositions of the present invention preferably contain a synergist, such as an aminoacrylate or a dimethylaminobenzoic acid ester, as is well known in the art. Preferably the synergist will be a dimethylaminobenzoic acid ester in the case of a printing ink or an aminoacrylate in the case of a varnish. Some inks, such as those used in flexographic printing applications may contain both amine types.

The amounts of the radiation-curable monomer or oligomer, photoinitiator, synergist and optional colorant will vary according to the type of varnish or ink, the particular equipment to be used to apply it and the application.

However, typically, the amount of photoinitiator plus synergist is from 1% to 20% by weight of the total composition.

The multi-functional initiators of formula (I), when used in varnishes and inks, typically comprise, as additional components to those referred to above, one or more of pigments, waxes, stabilisers, and flow aids, for example as described in "Printing Ink Manual", fourth edition, Leach R. H. et al. (eds.), Van Nostrand Reinhold, Wokingham, (1988), the disclosure of which is incorporated herein by reference.

The present invention will be further illustrated by reference to the following non-limiting examples. In the formulae given in the Examples, n represents a degree of polymerisation, which may be calculated approximately from the molecular weight (MW) of the compound.

COMPARATIVE EXAMPLE 1

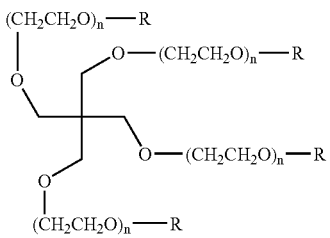

-continued

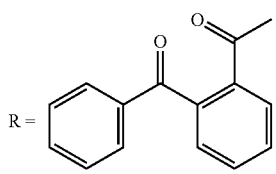

R =

79.1 g (0.35 mols) 2-benzoylbenzoic acid and 79.6 g (0.1 mols) ethoxylated pentaerythritol (15/4 ethoxylation level, MW 796) were azeotropically refluxed in 500 ml toluene using 3.0 g methanesulphonic acid catalyst for 24 hours. The solution was then filtered, and all solvent was removed using a rotary evaporator under vacuum, to yield a pale straw-coloured liquid. The product was characterised by HPLC and GPC.

COMPARATIVE EXAMPLE 2

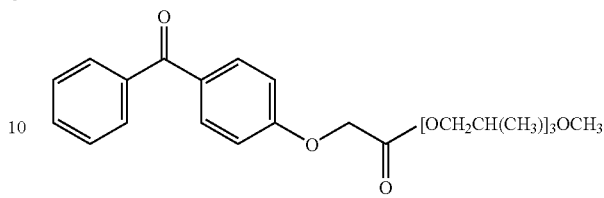

20.16 g (0.079 mols) 4-carboxymethoxybenzophenone and 15.45 g (0.075 mols) tripropylene glycol monomethyl ether were azeotropically refluxed in 300 ml toluene with 0.8 g p-toluenesulphonic acid catalyst for 6.5 hours. The solution was then washed twice with 200 ml 0.1 M aqueous sodium hydroxide and twice with 200 ml deionised water. The toluene layer was then dried over anhydrous magnesium sulphate and filtered before removing all solvent under vacuum using a rotary evaporator, to give 24.8 g of a light yellow coloured liquid.

Product analysed by HPLC.

COMPARATIVE EXAMPLE 3

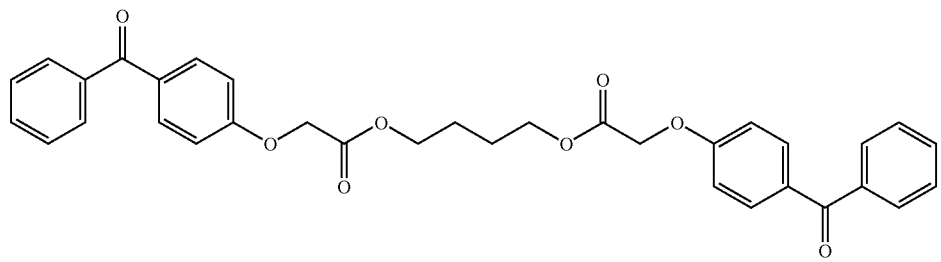

10.75 g (0.042 mols) 4-carboxymethoxybenzophenone and 1.8 g (0.02 mols) 1,4-butanediol were azeotropically refluxed in 150 ml toluene with 0.4 g p-toluene-sulphonic acid catalyst for 7 hours. On cooling, a solid precipitated out which was collected by filtration. This crude product was then re-dissolved in dichloromethane and washed twice with 200 ml aqueous 0.1 M sodium hydroxide and twice with 200 ml deionised water. After drying over anhydrous magnesium sulphate and filtering, all the solvent was removed under vacuum on a rotary evaporator to yield 8.1 g of a white solid.

Product analysed by HPLC.

COMPARATIVE EXAMPLE 4

Solubility Of Product Of Comparative Example 3

The solubility of the product of Comparative Example 3 was assessed in a typical UV curing overprint varnish formulation comprising 25% of an epoxy acrylate oligomer (CN104A80 ex Cray-Valley), 8% of an aminoacrylate synergist (Actilane 715 ex Akcros Chemicals) with the balance being the monomer glycerol propoxylate triacrylate (GPTA). Varnishes containing photoinitiator levels of 1, 2, 3, 4, 5, 6 and 7% were prepared and heated on a hot plate stirrer, with a temperature of 100° C. being required to dissolve all the photoinitiator. After being left at room temperature for 72 hours, the photoinitiator had come back out of solution in all samples except that containing only 1% photoinitiator.

COMPARATIVE EXAMPLE 5

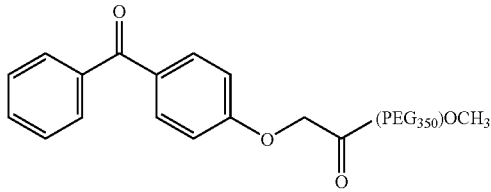

14.08 g (0.055 mols) 4-carboxymethoxybenzophenone and 17.5 g (0.05 mols) polyethylene glycol 350 monomethyl ether were azeotropically refluxed in 200 ml toluene with 0.6 g p-toluenesulphonic acid catalyst for 7.5 hours. The solution was then washed twice with 200 ml aqueous 0.1 M sodium hydroxide and once with 200 ml deionised water. After drying over anhydrous magnesium sulphate and filtering, all the solvent was removed under vacuum on a rotary evaporator to yield 23.56 g of low viscosity pale yellow liquid.

Product analysed by HPLC.

EXAMPLE 1

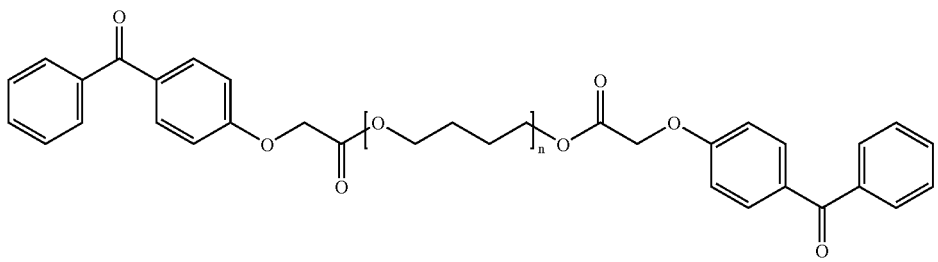

179.2 g (0.7 mols) 4-carboxymethoxybenzophenone and 87.5 g (0.35 mols) poly-tetrahydrofuran (average MW 250) were azeotropically refluxed in 2500 ml toluene with 3.0 g p-toluenesulphonic acid catalyst for 11 hours. The solution was then washed twice with 500 ml 0.1 M aqueous sodium hydroxide and twice with 500 ml deionised water. The solution was then azeotroped to dryness and then all solvent stripped under vacuum using a rotary evaporator, to yield 244.6 g of a light straw-coloured liquid.

Product analysed by HPLC.

EXAMPLE 2

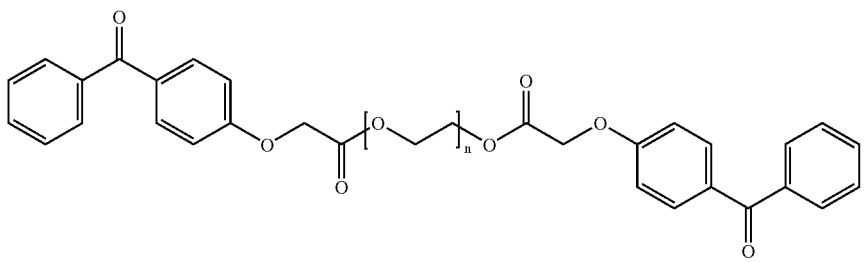

26.88 g (0.105 mols) 4-carboxymethoxybenzophenone and 10.0 g (0.05 mols) polyethylene glycol (average MW 200) were azeotropically refluxed in 300 ml toluene with 0.4 g p-toluenesulphonic acid catalyst for 5.5 hours. The solution was then washed twice with 250 ml 0.1 M aqueous sodium hydroxide and twice with 250 ml deionised water. The solution was then dried over anhydrous magnesium sulphate, filtered, and then all solvent stripped under vacuum using a rotary evaporator to yield 30.5 g of a light straw-coloured high viscosity oil.

EXAMPLE 3

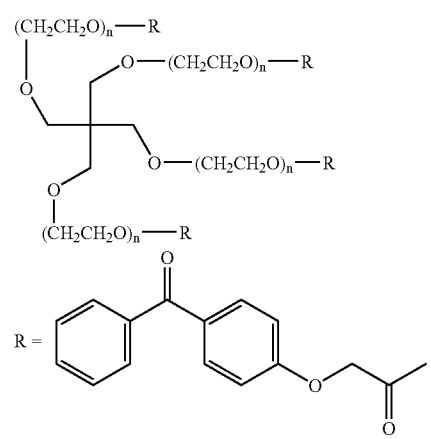

17.92 g (0.07 mols) 4-carboxymethoxybenzophenone and 11.52 g (0.02 mols) pentaerythritol ethoxylate (average MW 576) were azeotropically refluxed in 200 ml toluene with 0.5 g p-toluenesulphonic acid catalyst for 10 hours. The solution was then washed twice with 250 ml 0.1 M aqueous sodium hydroxide and once with 250 ml deionised water. The solution was then dried over anhydrous magnesium sulphate, filtered, and then all solvent stripped under vacuum using a rotary evaporator to yield a light straw-coloured high viscosity oil.

Product analysed by HPLC.

EXAMPLE 4

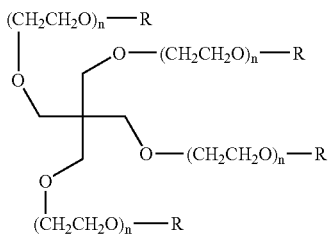

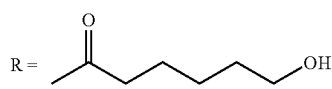

26.4 g (0.1 mols) pentaerythritol ethoxylate (average molecular weight 264) and 102.6 g (0.9 mols) ε-caprolactone were refluxed in 300 ml toluene with 0.1 g BHT (butylated hydroxytoluene) and 6 drops of titanium isopropoxide for 12.5 hours. All solvent was then stripped under vacuum using a rotary evaporator, to yield a pale-coloured low viscosity liquid. GPC analysis confirmed a molecular weight in the region of 2000 amu.

EXAMPLE 5

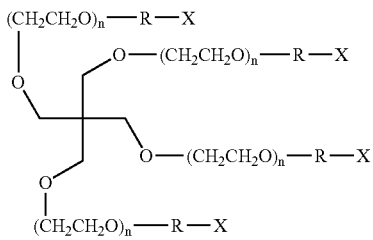

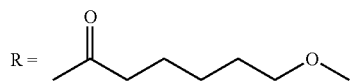

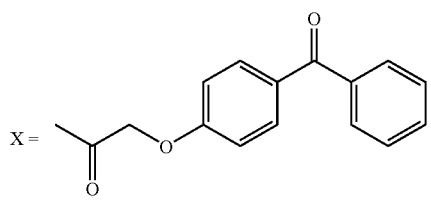

44 g (0.172 mols) 4-carboxymethoxybenzophenone and 55.4 g of the material prepared in Example 4 were azeotropically refluxed in 500 ml toluene with 0.5 g p-toluenesulphonic acid catalyst for 6 hours. The solution was then washed twice with 500 ml 0.1 M aqueous sodium hydroxide and once with 250 ml deionised water. The solution was then azeotroped to dryness, filtered, and then all solvent stripped under vacuum using a rotary evaporator, to yield 87 g of a colourless low viscosity oil.

EXAMPLE 6

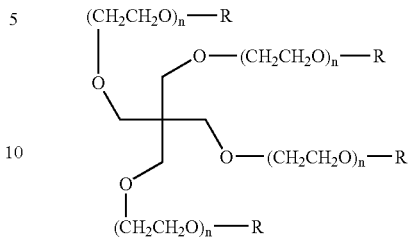

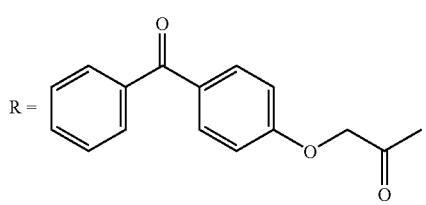

17.92 g (0.07 mols) 4-carboxymethoxybenzophenone and 15.92 g (0.02 mols) pentaerythritol ethoxylate (average MW 796) were azeotropically refluxed in 250 ml toluene with 0.3 g p-toluenesulphonic acid catalyst for 4 hours. The solution was then washed twice with 200 ml 0.1 M aqueous sodium hydroxide and once with 200 ml deionised water. The solution was then dried over anhydrous magnesium sulphate, filtered, and then all solvent stripped under vacuum using a rotary evaporator to yield a light straw-coloured high viscosity oil.

Product analysed by HPLC.

EXAMPLE 7

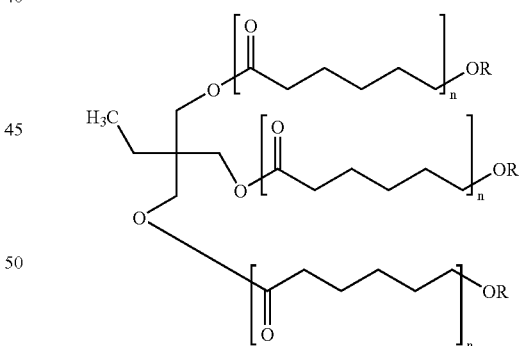

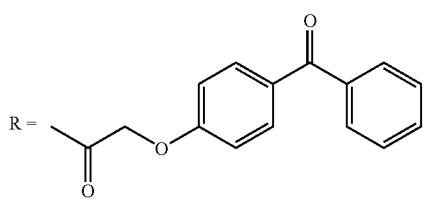

17.92 g (0.07 mols) 4-carboxymethoxybenzophenone and 18 g (0.02 mols) Tone 0310 (ex Union Carbide) were azeotropically refluxed in 250 ml toluene with 0.3 g p-toluenesulphonic acid catalyst for 10 hours. The solution was then washed twice with 200 ml 0.1 M aqueous sodium hydroxide and once with 200 ml deionised water. The solution was then dried over anhydrous magnesium sulphate, filtered, and then all solvent stripped under vacuum using a rotary evaporator to yield a light straw-coloured medium viscosity oil.

EXAMPLE 8

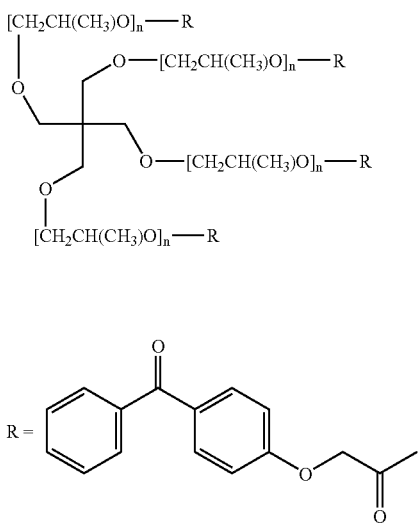

25.6 g (0.1 mols) 4-carboxymethoxybenzophenone and 15.7 g (0.025 mols) pentaerythritol propoxylate (average molecular weight 629) were azeotropically refluxed in 300 ml toluene with 0.8 g R-toluenesulphonic acid catalyst for 10 hours. The solution was then washed twice with 250 ml 0.1 M aqueous sodium hydroxide and twice with 250 ml deionised water. The solution was then dried over anhydrous magnesium sulphate, filtered, and then all solvent stripped under vacuum using a rotary evaporator to yield a yellow high viscosity oil.

EXAMPLE 9

Comparison Of Cure Performance

Each of the test photoinitiators prepared as described in the above Examples and Comparative Examples was made up into a UV curable varnish formulation comprising;

7% photoinitiator

8% aminoacrylate synergist (Actilane 715 ex Akcros)

25% epoxy acrylate oligomer (CN104 A80 ex Cray-Valley)

60% multifunctional monomer, GPTA (glycerol propoxylate triacrylate)

The varnish formulations were printed onto Leneta charts using a number 0 K bar and cured at 100 m/min using a single medium pressure mercury arc lamp operating at a power of 140 W/inch (56 W/cm). The number of passes under the lamp in order to effect good surface and through cure was recorded. Note that the lamp power was deliberately set to approximately half of maximum power in order to achieve good differentiation of results. The results are shown in the following Table.

TABLE 1

| Photoinitiator | Number of passes to achieve full cure |
|---|---|
| Benzophenone | 4 |
| Speedcure MBB | 5 |
| IRR261 | 7 |
| Comparative example 1 | 8 |
| Comparative example 2 | 7 |
| Comparative example 5 | 7 |
| Example 1 | 5 |
| Example 2 | 6 |
| Example 3 | 5 |
| Example 5 | 6 |
| Example 6 | 6 |
| Example 7 | 7 |
| Example 8 | 6 |

These results illustrate that the compounds of the present invention are at least as fast curing as those of the comparative examples. All of the compounds are also at least as fast curing as the most commonly used benzophenone alternative (acrylated benzophenone, IRR261) and, in two cases, are as fast curing as the most reactive of the benzophenone alternatives (Speedcure MBB).

All examples have very low cured odour in comparison to benzophenone. All examples also have a comparable level of yellowing on cure.

EXAMPLE 10

Comparison of Reaction Rates (a) Benzoyl Benzoic Acid Based Multi-Functional Photoinitiator

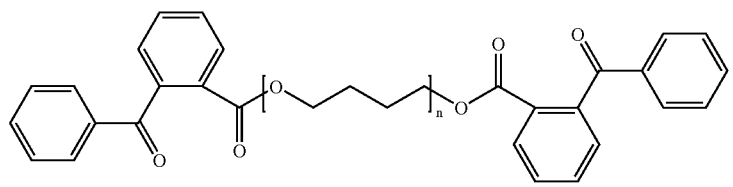

6.78 g (0.03 mols) 2-benzoylbenzoic acid and 3.75 g (0.015 mols)) poly-tetrahydrofuran (average MW 250) were azeotropically refluxed in 150 ml toluene using 0.1 g p-toluenesulphonic acid catalyst for 23.5 hours. The solution was periodically sampled for analysis.

(b) Carboxymethoxybenzophenone Based Multi-Functional Photoinitiator

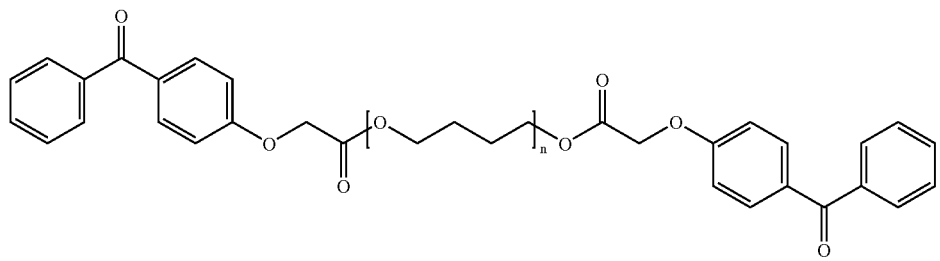

7.68 g (0.03 mols) 4-carboxymethoxybenzophenone and 3.75 g (0.015 mols)) poly-tetrahydrofuran (average MW 250) were azeotropically refluxed in 150 ml toluene using 0.1 g p-toluenesulphonic acid catalyst for 23.5 hours. The solution was periodically sampled for analysis.

(c) Analysis

Both reactions were done side-by-side. Samples of both reactions were taken and analysed by HPLC, where the chromatograms generated at 300 nm were divided into three distinct regions; acid functional benzophenone starting material, monofunctional esterified product and difunctional esterified product. A graph of the formation of the difunctional esterified product for each benzophenone acid type is shown in the attached FIG. 1.

Clearly the aliphatic carboxylic acid group on the benzophenone in the compounds of the present invention esterified significantly more readily than aromatic carboxylic acids such as that on 2-benzoylbenzoic acid.

EXAMPLE 11

Photoinitiator Contact Migration Analysis

A varnish formulation was prepared based on the following formulation:

| | |
|---|---|
| Epoxy acrylate oligomer, CN104A80 from Cray-Valley | 25% |
| Glycerol propoxylate triacylate (GPTA) | 59.9% |
| Aminoacrylate synergist, Actilane 715 ex Cognis | 8% |
| Tegorad 2500 slip additive | 0.1% |
| Photoinitiator | 7% |

The formulations were printed onto "Incada Silk 260 gsm" cartonboard substrate from Iggesund using a no. 0 "K bar". The prints were cured with 3 passes at 80 m/minute under a 280 W/inch medium pressure mercury arc lamp operating at full power.

The print samples were then subjected to a contact migration analysis procedure where the cured varnish is in contact with a filter paper susceptor and then sandwiched each side by aluminium foil. A number of these sandwiches were arranged in a stack and kept under a pressure of 10 tons for 72 hours in a "Specac".

The susceptor was then soaked for 24 hours in acetonitrile to re-dissolve any migrated photoinitiator. This was then quantified using HPLC and expressed in terms of grams of photoinitiator per unit area of print.

Levels of photoinitiator contact migration are shown in Table 2;

TABLE 2

Contact migration results for various photoinitiators

| Photoinitiator | Photoinitiator functionality | Contact migration onto paper (mg/m2) |
|---|---|---|
| Benzophenone | 1 | 12 |
| Speedcure MBB | 1 | 15 |
| Comparative example 5 | 1 | 6.4 |
| Example 1 | 2 | 1.03 |
| Example 3 | 4 | 0.10 |

The results in Table 2 clearly demonstrate that the multifunctional photoinitiators of the present invention have a significantly lower tendency to migrate than commercially available monofunctional photoinitiators such as benzophenone and Speedcure MBB. The photoinitiators of the present invention also have a significantly lower tendency to migrate than polymeric monofunctional photoinitiators such as that of Comparative Example 5, indicating that the higher photoinitiator functionality is more important than polymeric groups in achieving low migration.

EXAMPLE 12

Photoinitiator Vapour Phase Migration Analysis

Samples of cured print were prepared as described in Example 11 for the same samples. 50 cm$^2$ samples of these were placed in a Petri dish and covered with 1.0 g of Tenax. This was heated to 180° C. for 10 minutes and the Tenax was then extracted with diethyl ether before quantifying the photoinitiator present by HPLC.

Levels of photoinitiator vapour phase migration are shown in Table 3;

TABLE 3

Vapour phase migration results for photoinitiators

| Photoinitiator | Photoinitiator functionality | Vapour phase migration onto paper (mg/m2) |
|---|---|---|
| Benzophenone | 1 | 50 |
| Speedcure MBB | 1 | 144 |

TABLE 3-continued

Vapour phase migration results for photoinitiators

| Photoinitiator | Photoinitiator functionality | Vapour phase migration onto paper (mg/m2) |
|---|---|---|
| Comparative example 5 | 1 | =<21 |
| Example 1 | 2 | Not detected* |
| Example 3 | 4 | Not detected** |

*Detection limit ~ 1.0 mg/m$^2$
**Detection limit ~ 0.1 mg/m$^2$

The results in Table 3 demonstrate that the multifunctional photoinitiators of the present invention exhibit very low vapour phase migration (not detected) in comparison to commercially available monofunctional photoinitiators such as benzophenone and Speedcure MBB. Comparative Example 5 also demonstrates significantly lower vapour phase migration compared to benzophenone and Speedcure MBB, but although it was detected, co-elution with another component prevented accurate quantification.

The invention claimed is:

1. Photoinitiator compounds of formula (I):

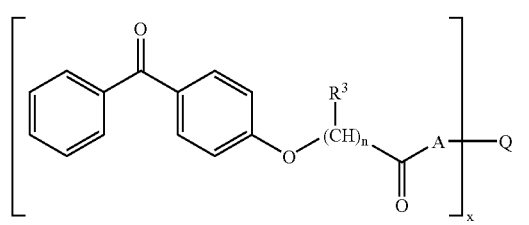

(I)

where:
n is a number from 1 to 6
$R^3$ represents a hydrogen atom, a methyl group or an ethyl group, and, when n is greater than 1, the groups or atoms represented by $R^3$ may be the same as or different from each other;
A represents a group of formula —[O(CHR$^2$CHR$^1$)$_a$]$_y$—, —[O(CH$_2$)$_b$CO]$_y$—, or —[O(CH$_2$)$_b$CO]$_{(y-1)}$—[O(CHR$^2$CHR$^1$)$_a$]—, where:
one of $R^1$ and $R^2$ represents a hydrogen atom and the other represents a hydrogen atom, a methyl group or an ethyl group;
a is a number from 1 to 2;
b is a number from 4 to 5;
Q is a residue of a polyhydroxy compound having 2 to 6 hydroxy groups; and
X is a number greater than 1 but no greater than the number of available hydroxyl groups in Q;
when x is a number greater than 1 but no greater than 2, y is a number from 1 to 10;
or
when x is a number greater than 2, y is a number from 3 to 10;
and esters thereof.

2. Compounds according to claim 1, in which n is 1.

3. Compounds according to claim 2, in which $R^3$ represents a hydrogen atom.

4. Compounds according to claim 1, in which n is a number from 2 to 6 and one group $R^3$ represents a hydrogen atom, or a methyl or ethyl group and the other or others of $R^3$ represent hydrogen atoms.

5. Compounds according to claim 1, in which x is 2 and y is a number from 1 to 10.

6. Compounds according to claim 1 in which y is a number from 3 to 10.

7. Compounds according to claim 1 in which A represents a group of formula —[O(CHR$^2$CHR$^1$)$_a$]$_y$—where a is an integer from 1 to 2, and y is a number from 3 to 10.

8. Compounds according to claim 1 in which A represents a group of formula —[OCH$_2$CH$_2$]$_y$—, —[OCH$_2$CH$_2$CH$_2$CH$_2$]$_y$—or —[OCH(CH$_3$)CH$_2$]$_y$—, where y is a number from 3 to 10.

9. Compounds according to claim 1 in which A represents a group of formula —[O(CH$_2$)$_b$CO]$_y$—, where b is a number from 4 to 5 and y is a number from 3 to 10.

10. Compounds according to claim 1 in which A represents a group of formula —[O(CH$_2$)$_b$CO]$_{(y-1)}$—[O(CHR$^2$CHR$^1$)$_a$]—, where a is a number from 1 to 2, b is a number from 4 to 5 and y is a number from 3 to 10.

11. Compounds according to claim 1, in which y is a number from 3 to 6.

12. Compounds according to claim 1, in which the residue Q—(A—)$_x$ has a molecular weight no greater than 2000.

13. Compounds according to claim 12, in which the residue Q—(A—)$_x$ has a molecular weight no greater than 1200.

14. Compounds according to claim 13, in which the residue Q—(A—)$_x$ has a molecular weight no greater than 1000.

15. Compounds according to claim 14, in which the residue Q—(A—)$_x$ has a molecular weight no greater than 800.

16. Compounds according to claim 1, in which Q is a residue of ethylene glycol, propylene glycol, butylene glycol, glycerol, trimethylolpropane, di-trimethylolpropane, pentaerythritol or di-pentaerythritol.

17. An energy curable liquid composition, comprising:
(a) a polymerisable component which is at least one ethylenically unsaturated monomer or oligomer; and
(b) a photoinitiator according to claim 1.

18. An energy curable liquid composition according to claim 17, which is a varnish.

19. An energy curable liquid composition according to claim 17, which is a printing ink.

20. A process for preparing a cured polymeric composition by exposing a composition according to claim 17 to radiation.

21. A process according to claim 20, in which the radiation is ultraviolet.

* * * * *